United States Patent [19]

Babler

[11] Patent Number: 5,191,127

[45] Date of Patent: Mar. 2, 1993

[54] GLYOXAL DERIVATIVES AND METHOD FOR MAKING THE SAME

[75] Inventor: James H. Babler, Chicago, Ill.

[73] Assignee: Loyola University of Chicago, Chicago, Ill.

[21] Appl. No.: 743,074

[22] Filed: Aug. 13, 1991

[51] Int. Cl.$^5$ .................... C07C 43/30; C07C 43/32
[52] U.S. Cl. ..................... 568/591; 568/598; 568/600; 568/601
[58] Field of Search ............... 568/592, 594, 591, 598, 568/600, 601

[56] References Cited

FOREIGN PATENT DOCUMENTS 246646 of 1987 European Pat. Off. .
316672 of 1987 European Pat. Off. .

OTHER PUBLICATIONS

Babler, *Synthetic Communications*, 17(1), (1987), pp. 77-84.
Bernard, et al., *Synthetic Communications*, 17(15), (1987), pp. 1807-1814.
Bestmann, et al., *Reaktionen mit Phosphinalkylenen*, 44 (1983) pp. 3264-3266.
Bou, et al., *Tetrahedron*, vol. 37 (1981) pp. 1441-1449.
*Chem. Abstracts*, vol. 57:10037h, (1962) p. 10038.
Kliegman, et al., *J. Org. Chem.*, vol. 38, No. 3, (1973) pp. 556-560.
Sangsari, et al., *Synthetic Communications*, 18(12), (1988) pp. 1343-1348.
Schlittler, et al., *Helvetica Chimica Acta*, vol. XXXI, (1948) pp. 914-924.
Stambouli, et al., *Bulletin de la Societe Chimique de France*, (1988) No. 1, pp. 95-100.
Stambouli, et al., *Tetrahedron Letters*, vol. 27, No. 35, (1986) pp. 4149-4152.

*Primary Examiner*—Jose G. Dees
*Assistant Examiner*—Joseph Conrad
*Attorney, Agent, or Firm*—Marshall, O'Toole, Gerstein, Murray & Bicknell

[57] ABSTRACT

This invention provides glyoxal derivatives and a method for making these derivatives. A particularly useful derivative, 1-chloro-1,2,2-trialkoxyethane, and a facile method for making these alpha-halo ethers are provided. The alpha-halo ethers are valuable intermediates in the manufacture of a variety of commercial compounds.

7 Claims, 3 Drawing Sheets

Fig. 3
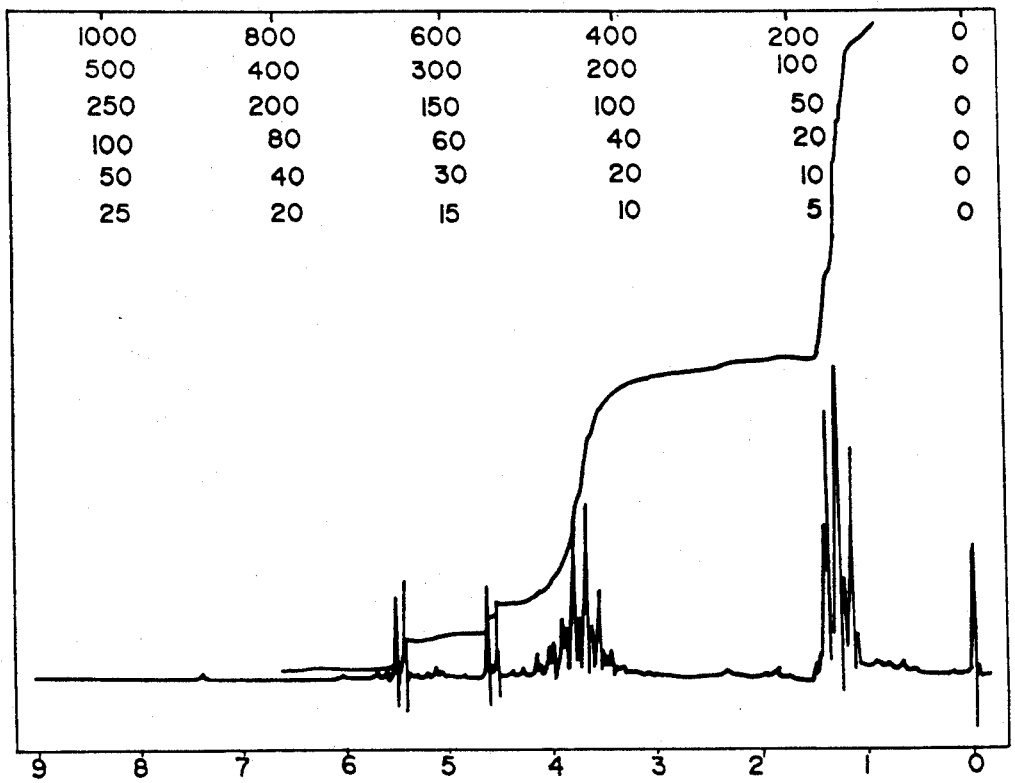
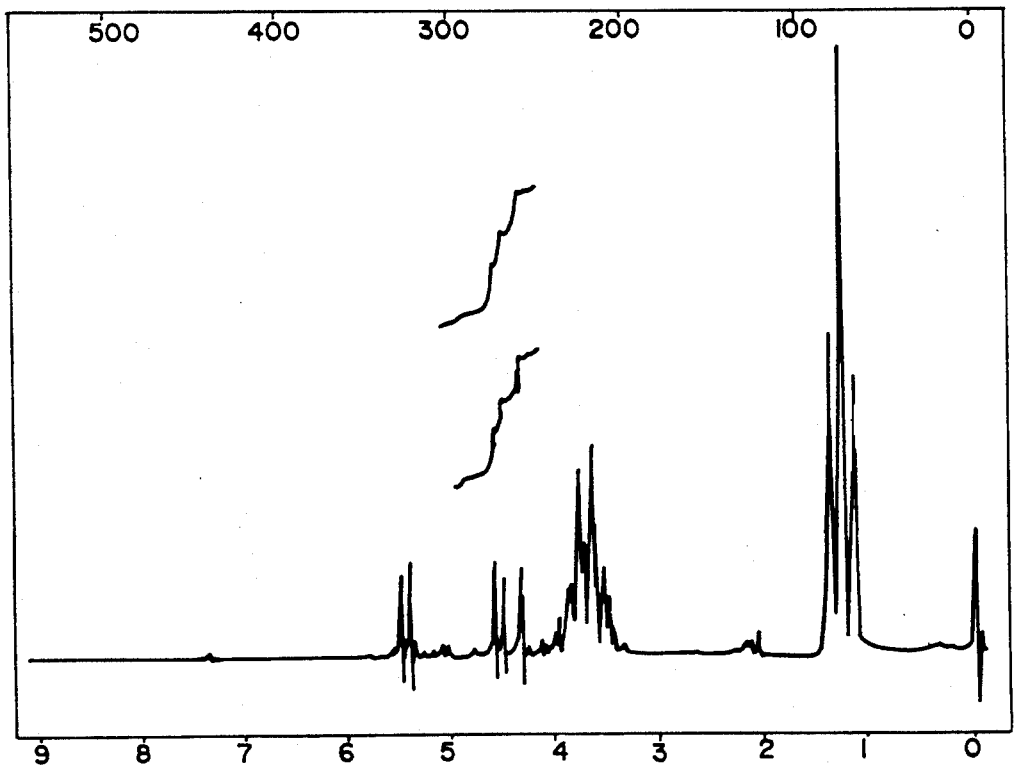
Fig. 4

GLYOXAL DERIVATIVES AND METHOD FOR MAKING THE SAME

FIELD OF THE INVENTION

The present invention relates to novel chlorotrialkoxyethane compounds and to a facile method for making these compounds. In addition, a method of using chlorotrialkoxyethane compounds as intermediates in the manufacture of other useful compounds is provided by the invention.

BACKGROUND OF THE INVENTION

Glyoxal, typically sold as a 40% aqueous solution, is an inexpensive chemical with a variety of industrial uses, most importantly for treatment of cellulosic textiles. The known bis(dialkyl acetal) derivatives of glyoxal of the formula:

(RO)$_2$CHCH(OR)$_2$ are readily prepared in high yield (80–100%, depending on the nature of "R"). In contrast, the corresponding monoacetal derivatives of glyoxal of the formula:

(RO)$_2$CHCHO are much more difficult to prepare although the monoacetal derivatives of glyoxal are potentially versatile intermediates in organic synthesis. Current industrial-scale preparations of monoacetal derivatives have generally been avoided due to the difficulties inherent in previously-known routes which often require the use of hazardous reagents, lengthy reaction sequences, expensive reagents, and/or which result in complex product mixtures.

Different processes for making monoacetal derivatives of glyoxal have been reported. For example, ozonolysis of 3,3-dialkoxypropenes (acrolein dialkyl acetals) at low temperatures, followed by subsequent reduction with triphenylphosphine is reported to give a dialkoxy aldehyde, H. J. Bestmann and P. Erman, Chem. Ber., 116:3264 (1983). A multi-step process that uses comparatively expensive specialty chemicals (e.g., 3-ethoxyacrylonitrile and N-bromosuccinimide) is also reported to give a dialkoxy aldehyde, J. H. Babler, Synth. Commun., 17:77 (1987). Oxidation of commercially available, but expensive, 2,2-diethoxy-1-ethanol (glycolaldehyde diethyl acetal) to give the dialkoxy aldehyde is reported by D. Bernard, A. Doutheau, and J. Gore, Synth. Commun. 17:1807 (1987).

Partial acetalization of aqueous glyoxal is reported by A. Stambouli et al., Bull. Soc. Chim. France, 95 (1988). Although this reported one-step method yields 2,2-dialkoxyethanals (i.e., monoacetal derivatives of glyoxal), careful monitoring of the reaction is required to avoid acetalization of both carbonyl groups of glyoxal; the yield of monoacetal product is only moderate (50–70%). A reported improvement for this type of acetalization reacts various 1,3-propanediol reagents with glyoxal in 1,2-dichloroethane at high temperatures, but the monoacetal derivatives obtained in this manner are isolated only after careful vacuum distillation and frequently several repetitions of the high-temperature process may be necessary to obtain an acceptable yield. See European Patent 316,672 (Nov. 4, 1988).

Finally, a single monoacetal glyoxal derivative, (CH$_3$O)$_2$CHCHCl(OCH$_3$), has been reported by Bou et al., Tetrahedron, 37:1441–1449 (1981). This derivative was obtained as a minor component of a reaction mixture which resulted in the formation of the sought-after dichloro compound (CH$_3$O)ClCHCHCl(OCH$_3$) as the major product.

As noted above, monoacetal derivatives of glyoxal have potential use in a variety of synthetic processes. For example, the compound (RO)$_2$CHCHO is reportedly used in the manufacture of vitamin A. See, European Patents 246,646 (May 21, 1987) and 316,672 (Nov. 4, 1988). Alpha-halo ethers derived from glyoxal, due to the high reactivity of the carbon-chlorine bond in such compounds in nucleophilic substitution reactions, are attractive intermediates in the manufacture of several known industrial compounds, as well as prospective intermediates in the manufacture of various known or novel specialty organic chemicals.

Another example of the synthetic utility of 1-chloro-1,2,2-trialkoxyethanes involves their reaction with primary amines. For example, reacting these copounds with benzylamine gives the intermediate (RO)$_2$CHCH=NCH$_2$Ph, in high yield. This intermediate may be readily converted to isoquinoline, a heterocyclic compound with extensive industrial uses, by treatment with aqueous acid as reported by E. Schlittler and J. Müller, Helv. Chim. Acta., 31:914 (1948). Glyoxal monoacetal derivatives may also be used to prepare, various alpha, beta-unsaturated aldehydes, unsymmetrically-substituted 1,3-dienes, and numerous other compounds of the general structure W=CH—CH=Z (W≠Z).

In view of the broad application of monoacetal derivatives of glyoxal to synthetic methodology, a need exists for a facile method of preparing these derivatives using inexpensive, readily-available reagents and solvents.

SUMMARY OF THE INVENTION

The present invention provides a process for preparing monoacetal derivatives of glyoxal as well as other useful related compounds. Besides the high overall yields, up to about 90% from aqueous glyoxal, this method offers two additional advantages: (a) differentially functionalized two-carbon building blocks, not readily accessible from glyoxal monoacetal derivatives, and (b) novel 1-chloro-1,2,2-trialkoxyethanes that are reasonably stable compared to known monoacetal derivatives of glyoxal which are susceptible to polymerization during purification or subsequent reactions. The alpha-chloro ethers provided by the present invention may be converted to other useful compounds (e.g., isoquinoline and acetal derivatives of aminoacetaldehyde) without the need for generating unstable glyoxal monoacetal derivatives themselves.

A first step of the method of this invention includes conversion of aqueous glyoxal to bisacetal derivatives, (RO)$_2$CHCH(OR)$_2$, using primary and secondary alcohols. Preferred alcohols include ethyl alcohol, allyl alcohol (2-propen-1-ol), 1-butanol, and cyclohexanol. Other simple monohydric alcohols are also suitable (e.g., methyl alcohol, 1-propanol, isopropyl alcohol and isobutyl alcohol). Typically, yields for the acetal formation step are high, ranging from 80 to 100%.

(Step 1)

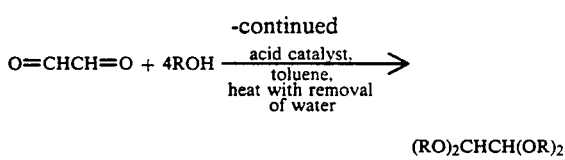

(RO)₂CHCH(OR)₂

Specific yields of bisacetal in this first step are as follows: when R is butyl, about 97%; when R is methyl or ethyl, about 80% (F. Chastrette et al., *Synth. Commun.* 18:1343 (1988); and when R is allyl, about 83% (Belgian Patent 609,343 (Apr. 19, 1962), and *Chem. Abstracts.* 57:10037h (1962)).

A second step of the method of this invention includes conversion of the bisacetal derivatives of glyoxal to a 1-chloro-1,2,2-trialkoxyethane using hydrogen chloride, preferably as a catalyst, in the presence of one equivalent of a chloride reagent such as acetyl chloride or thionyl chloride which continuously regenerates HCl as the reaction proceeds. Unexpectedly, no 1,2-dichloro-1,2-dialkoxyethanes were obtained, even in the presence of an excess of acetyl chloride or similar reagents.

(Step 2)

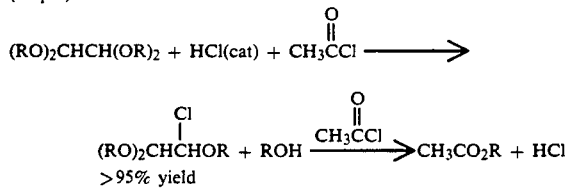

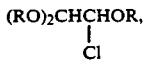

The hydrogen chloride that is needed to initiate the second step may be generated by addition of a catalytic amount of ROH or H₂O to a chloride-containing reagent, such as acetyl chloride or thionyl chloride. Carboxylic acid chlorides are preferred because these compounds scavenge the alcohol which is liberated as the reaction proceeds, thereby continuously regenerating the necessary hydrogen chloride.

When acetyl chloride is used for this step, no aqueous work-up is needed; only simple distillative removal of volatile organic material, $CH_3CO_2R$, at slightly reduced pressure is needed in order to isolate the desired 1-chloro1,2,2-trialkoxyethanes. Alternatively, it is possible to add aqueous sodium bicarbonate to the crude reaction mixture and proceed to the next step (conversion to glyoxal monoacetal derivatives) without removal of the acetate ester.

Although acetyl chloride or thionyl chloride are preferred reagents for effecting the transformation of step 2, the following reagents may also be used (albeit with lower yields or prolonged reaction times): carboxylic acid chlorides such as propionyl chloride, crotonyl chloride, trimethylacetyl chloride, or benzoyl chloride; phosphorus trichloride or phosphorous oxychloride (POCl₃); chlorotrimethylsilane; sulfonic acid chlorides such as methanesulfonyl chloride; and sulfuryl chloride (SO₂Cl₂).

Alternatively, at least one equivalent of HCl gas may be bubbled into the reaction mixture if aprotic solvents are used. For example, hydrogen chloride in various aprotic organic solvents such as dioxane, tetrahydrofuran, acetonitrile, ethyl acetate, toluene, methylene chloride, heptane, cyclohexane, or mixtures thereof may be used in the present method. Use of HCl in organic solvents not capable of scavenging the by-product alcohol, ROH, results in a product mixture containing a substantial amount (often 25%) of starting bisacetal which is presumably formed because the liberated alcohol can function as a weak nucleophile, displacing the chloro substitutent in the intermediate compound

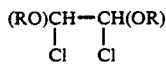

produced by the present method.

The chlorination step is generally conducted at room temperature, but proceeds rapidly at 0° C. in sulfuryl chloride. Use of certain chloride containing reagents such as benzoyl chloride or methanesulfonyl chloride in this reaction results in a slower process and may necessitate gentle heating (i.e., 50°–100° C.).

Unexpectedly, analysis of the crude products of the present method by proton NMR spectrometry, even when excess of acetyl chloride or thionyl chloride are utilized, failed to detect any significant amount of the "dihalo" product, (RO)CH—CH(OR)
  |       |
  Cl      Cl which would not be useful in preparing monoacetal derivatives of glyoxal.

The fact that the present method results in the formation of only the alpha-halo ether is surprising in view of the transformation outlined below involving glyoxal bisacetal derivatives that was recently reported by A. Stambouli et al., *Tetrahedron Lett.*, 27:4149 (1986).

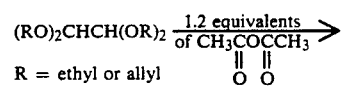

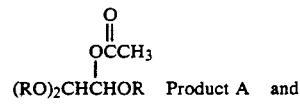

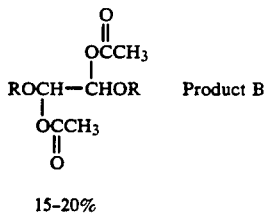

The formation of Product B (containing acetoxy groups at both carbon atoms) in a roughly statistical proportion was expected. When one treats a symmetrical compound containing two identical functional groups with only one equivalent of a reagent, a "statistical mixture" of products (i.e., approximately 50% of the monoderivatized product and 25% of the bisderivatized product) would be expected. The method of the present invention, however, provides substantially no dihaloethers.

In a third step of the present method, the chloride may be displaced by a nucleophile.

(Step 3)

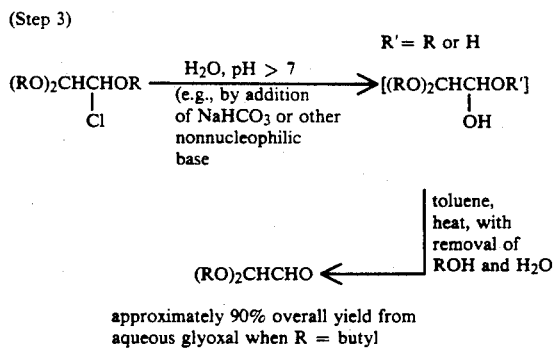

approximately 90% overall yield from aqueous glyoxal when R = butyl

For example, the displacement of chloride by water (hydroxide) is very facile, reaction being complete in less than one hour at 0° C. In order to increase the solubility of the alpha-chloro ether in the reaction mixture, organic solvents such as dimethylformamide, 1-methyl-2-pyrrolidinone, or tetrahydrofuran may be added to the reaction mixture. Prior to being heated in toluene, the initial reaction mixture includes a mixture of

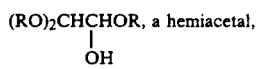

$(RO)_2CHCH(OH)_2$, the hydrate of glyoxal monoacetal, and $(RO)_2CHCHO$, glyoxal monoacetal. Heating then provides the monoacetal in high yield.

Other nucleophiles that are able to displace the chloride in these alpha-halo ethers include carboxylate anions, primary amines, nitrite salts, thiols, malonate, and cyanide.

An example illustrating the versatility of 1-chloro-1,2,2-trialkoxyethanes of the present invention is outlined below:

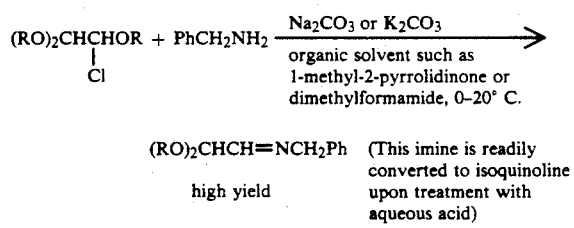

By avoiding formation of the rather unstable, known glyoxal monoacetal derivatives, this route to isoquinoline is a significant improvement over known routes. In an analogous manner, treatment of 1-chloro-1,2,2-trialkoxyethanes with sodium nitrite in a polar, aprotic solvent, after reduction of the intermediate, provides acetal derivatives of aminoacetaldehyde, which are used to prepare a variety of heterocycles important in the pharmaceutical industry.

Another use for monoacetal derivatives of glyoxal involves a crossed aldol reaction with propionaldehyde, a transformation that was published in *Liebigs Ann. Chem.*, (1976), as outlined below:

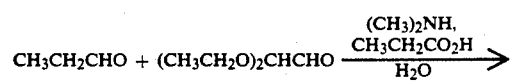

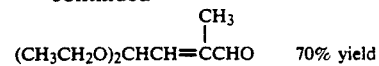

70% yield

The product is reported to be a useful intermediate in the manufacture of vitamin A. See European Patent 246,646 (May 21, 1987).

BRIEF DESCRIPTION OF THE DRAWINGS

FIG. 3 is an NMR spectrum of a chlorotrialkoxy glyoxal derivative prepared according to the procedure of Example IV.

FIG. 4 is an NMR spectrum of a mixture of glyoxal derivatives prepared according to Example IV.

DETAILED DESCRIPTION OF THE INVENTION

The following examples illustrate specific embodiments of the practice of the method of the present invention. Bisacetal derivatives of glyoxal prepared according to known procedures are described in Examples I, II, and III. The conversion of these bisacetal derivatives to 1-chloro-1,2,2-trialkoxyethanes is described in Examples IV-XVI. Displacement of the chloride in these 1-chloro-1,2,2-trialkoxyethanes by representative nucleophiles is described in Examples XVII, XVIII, and XIX.

EXAMPLE I

Preparation of Glyoxal Bis(Dibutyl Acetal)

Figure 1:
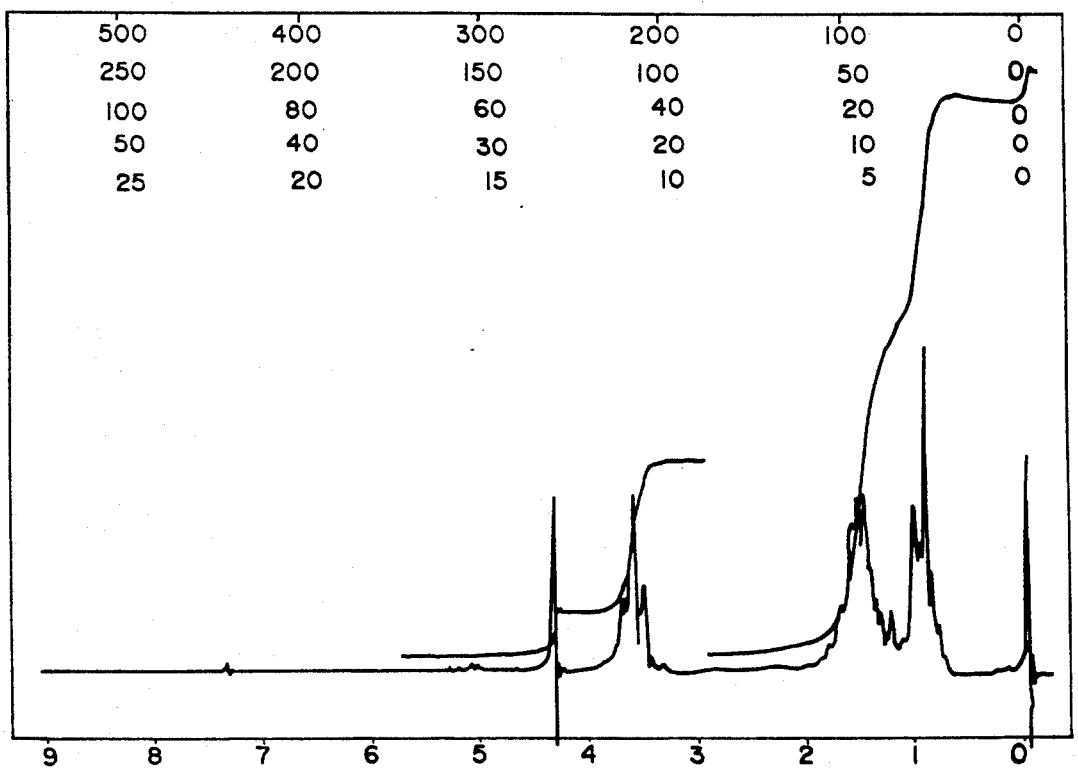
FIG. 1 is an NMR spectrum of a bis(dialkyl acetal) glyoxal derivative prepared according to the procedure of Example I.

A mixture containing 4.17 g (28.7 mmoles) of glyoxal (40 wt. % solution in water), 13.0 mLs (142 mmoles) of 1-butanol, and 175 mg (0.92 mmole) of p-toluenesulfonic acid monohydrate in 8.00 mLs of benzene was heated at reflux for 6.5 hours with continuous azeotropic removal of water. The cooled mixture was diluted with 25 mLs of ether and washed in successive order with saturated aqueous sodium bicarbonate (20 mLs) and saturated brine (20 mLs). The washed organic layer was then dried over anhydrous sodium sulfate and filtered. Removal of the volatile organic solvents under reduced pressure, followed by evaporative distillation, afforded 8.89 g (97% yield) of the named bisacetal: boiling point 118°-130° C. (bath temperature, 0.25 mm). The identity and purity of this bisactal were ascertained by proton NMR analysis. A copy of the NMR spectrum is provided in FIG. 1. A less pure sample of this compound has previously been prepared, using a modified procedure, by J. M. Kliegman and R. K. Barnes, *J. Org. Chem.*, 38:556 (1973).

EXAMPLE II

Preparation of Glyoxal Bis(Diethyl Acetal)

Figure 2:
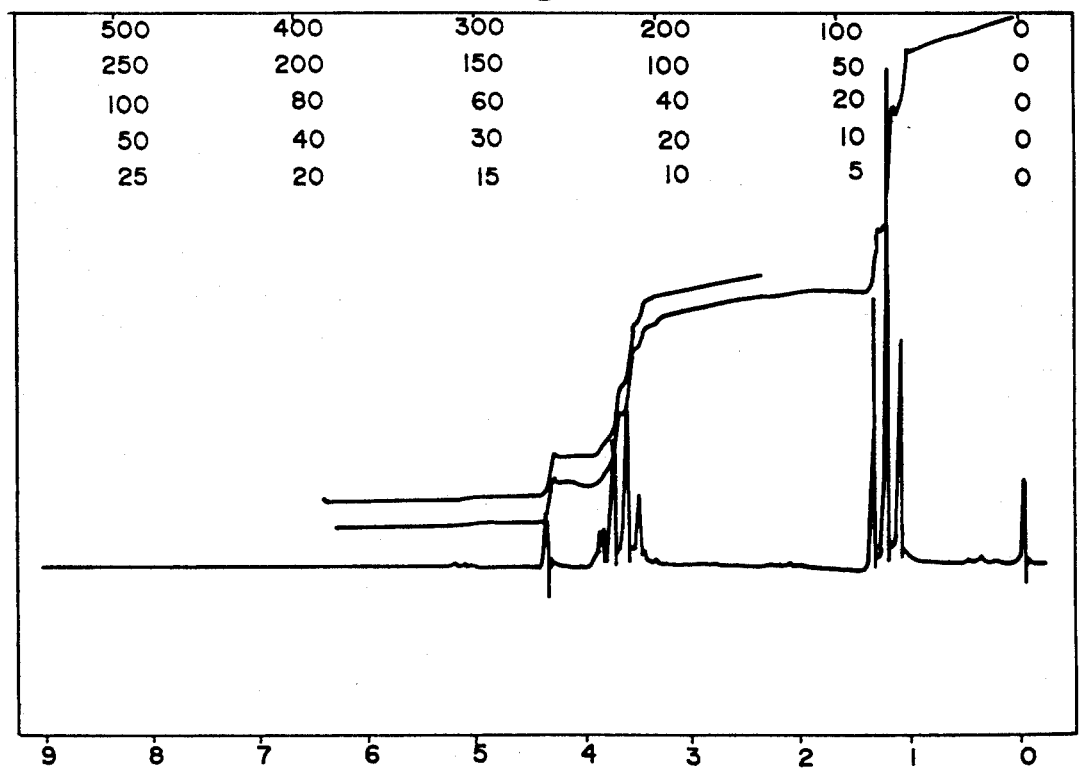
FIG. 2 is an NMR spectrum of a bis(dialkyl acetal) glyoxal derivative prepared according to the procedure of Example II.

A mixture containing 8.20 g (56.5 mmoles) of glyoxal (40 wt. % solution in water), 14.0 mLs (239 mmoles) of absolute ethanol, and 343 mg (1.8 mmoles) of p-toluenesulfonic acid monohydrate in 25 mLs of benzene was heated at reflux for 8 hours with continuous azeotropic removal of water. The cooled mixture was then concentrated under reduced pressure to a volume of approximately 15 mL, after which it was diluted with 10 mL of saturated aqueous sodium bicarbonate and 80 mL of 10% aqueous sodium chloride. The product was removed from the aqueous layer by extraction with methylene chloride (3×40 mL). The combined organic extracts were washed with 15% aqueous sodium chloride (80 mL), then dried over anhydrous sodium sulfate and filtered. Removal of the methylene chloride under reduced pressure, followed by fractional distillation, afforded 4.17 g (36% yield) of the named bisacetal: boiling point 80°–85° C. at 5 mm. The identity and purity of this bisacetal were ascertained by proton NMR analysis. A copy of the NMR spectrum is provided in FIG. 2. This same compound can be prepared in greater than 80% yield using the modified procedure of F. Chastrette et al., Synth. Commun., 18:1343 (1988).

EXAMPLE III

Preparation of Glyoxal Bis(Dicyclohexyl Acetal)

The reaction was conducted in the manner described in the procedure of Example I using the following reagents: 2.096 g (14.45 mmoles) of glyoxal (40 wt. % solution in water), 7.00 mL (67.3 mmoles) of cyclohexanol, 88 mg (0.46 mmole) of p-toluenesulfonic acid monohydrate, and 5.00 mL of benzene. Isolation of the product as described in the procedure of Example I, followed by evaporative distillation, afforded 5.83 g (95% yield) of the named bisacetal: boiling point 205°–212° C. (bath temperature, 0.30 mm).

EXAMPLE IV

Preparation of 1-Chloro-1,2,2-triethoxyethane Using Acetyl Chloride to Generate HCl In order to generate a small amount of hydrogen chloride, 8 mg (0.17 mmole) of absolute ethanol was added to a solution of 197 mg (0.955 mmole) of glyoxal bis(diethyl acetal) (produced in accordance with Example II) in 0.25 mL (3.52 mmoles) of freshly distilled acetyl chloride. On a larger scale, it would be necessary to use only slightly more than one equivalent of acetyl chloride to ensure complete reaction. Due to the high volatility of acetyl chloride, a large excess was used in this example in view of its relatively small scale. This mixture, protected from atmospheric moisture, was subsequently stirred at room temperature for 4.5 hours. Removal of the volatile organic material (ethyl acetate and excess acetyl chloride) under reduced pressure afforded 185 mg (98% yield) of the title compound. The identity and purity of this compound were ascertained by proton NMR analysis. A copy of the NMR spectrum is provided in FIG. 3.

A similar procedure was conducted without adding any ethyl alcohol. The reaction still proceeds since trace amounts of hydrogen chloride can be generated from acetyl chloride and adventitious water. However, proton NMR analysis of the crude product indicated the presence of 20–25% unreacted starting bisacetal. Thus, as expected, hydrogen chloride was shown to promote this reaction. A copy of the NMR spectrum is provided in FIG. 4. The presence of unreacted bisacetal is indicated by the singlet at approximately δ4.3.

EXAMPLE V

Figure 5:
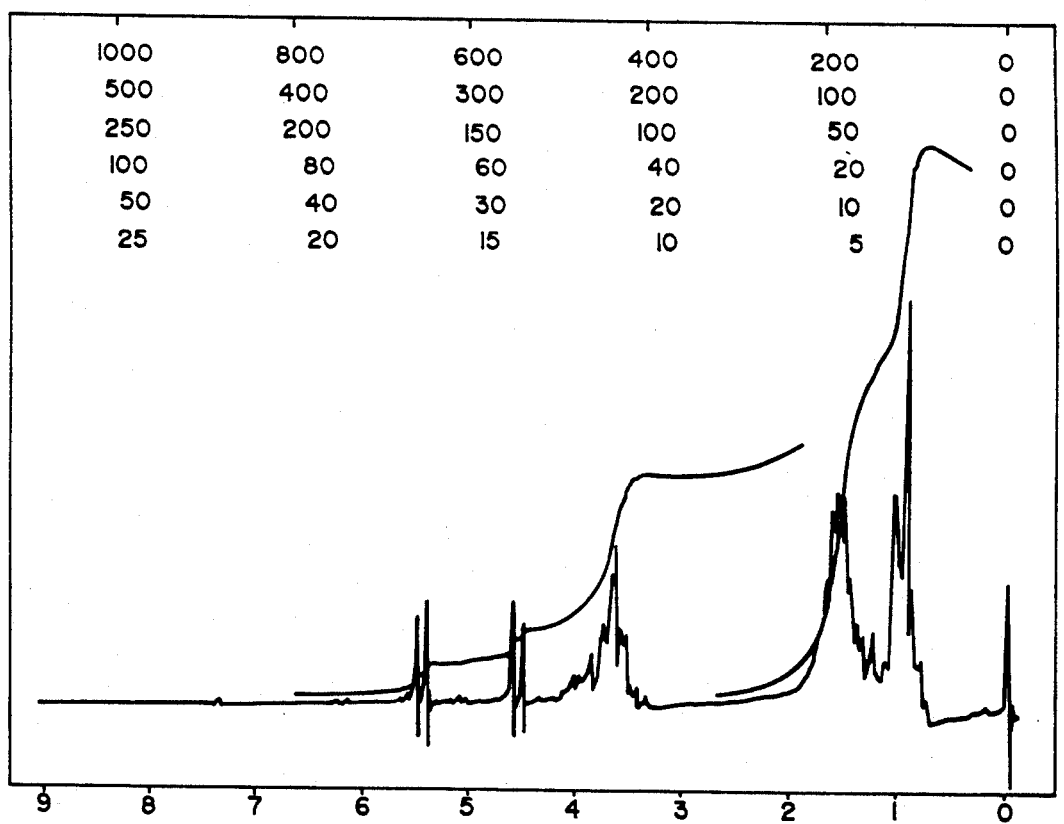
FIG. 5 is an NMR spectrum of a chlorotrialkoxy glyoxal derivative prepared according to the procedure of Example V.

Preparation of 1-Chloro-1,2,2-tributoxyethane Using Acetyl Chloride to Generate HCl In order to generate hydrogen chloride to initiate the reaction, 63 mg (0.85 mmole) of 1-butanol was added to a solution of 626 mg (1.97 mmoles) of glyoxal bis(dibutyl acetal) (produced in accordance with Example I) in 0.50 mL (7.04 mmoles) of freshly distilled acetyl chloride. This mixture, protected from atmospheric moisture, was subsequently stirred at room temperature for 2 hours. Removal of the volatile organic material (butyl acetate and excess acetyl chloride) under reduced pressure afforded 545 mg (98.6% yield) of the title compound. That the reaction had gone to completion and the product required no further purification were ascertained by proton NMR analysis. A copy of this NMR spectrum is provided in FIG. 5. No evidence is found in the spectra to indicate the presence of the dihalo derivative.

EXAMPLE VI

Preparation of 1-Chloro-1,2,2-triallyloxyethane Using Thionyl Chloride to Generate HCl A mixture of 1.98 g (7.77 mmoles) of glyoxal bis(diallyl acetal) commercially available from Aldrich Chemical Company, Milwaukee, Wis., and 100 mL (13.7 mmoles) of thionyl chloride, containing trace amounts of HCl generated from adventitious water and thionyl chloride, was heated at 65° C. (external oil bath temperature) for 8.5 hours, during which time the mixture was protected from atmospheric moisture. After cooling this mixture to room temperature, it was diluted with 20 mLs of 1:1 (volume/volume) pentane:ether, and the organic layer was washed in successive order with ice-cold 1M aqueous sodium hydroxide (20 mL) and saturated brine (20 mL). The washed organic layer was then dried over anhydrous sodium sulfate and filtered. Removal of the volatile organic material under reduced pressure afforded 1.80 g of product, shown by proton NMR analysis to be the title compound contaminated with approximately 15% unreacted starting bisacetal. Subsequent experiments demonstrated that this reaction goes to completion (in less time) if a catalytic amount of allyl alcohol is added to the initial reaction mixture to generate HCl in situ.

EXAMPLE VII

Preparation of 1-Chloro-1,2,2-tributoxyethane Using Phosphorus Trichloride to Generate HCl In order to generate hydrogen chloride to initiate the reaction, 18 mg (0.24 mmole) of 1-butanol was added to a mixture of 258 mg (0.81 mmole) of glyoxal bis(dibutyl acetal) (produced in accordance with Example I) and 0.25 mL (2.87 mmoles) of phosphorus trichloride. This mixture, protected from atmospheric moisture, was subsequently stirred at room temperature for 5 hours. After dilution of this mixture with 20 mL of 1:1 (volume/volume) pentane: ether, the product (239 mg) was isolated as described in the procedure of Example VI and shown by proton NMR analysis to be a 1:1 mixture of the desired alpha-chloro ether and unreacted starting bisacetal.

In a similar experiment conducted at 65° C. (external oil bath temperature) for 4 hours, using 253 mg of bisacetal, 0.25 mL of phosphorus trichloride, and no added 1-butanol, reaction to give the title compound was virtually complete.

EXAMPLE VIII

Preparation of 1-Chloro-1,2,2-tributoxyethane Using Gaseous Hydrogen Chloride in An Organic Solvent To 0.25 mL of 1,4-dioxane saturated with gaseous hydrogen chloride was added a solution of 178 mg (0.56 mmole) of glyoxal bis(dibutyl acetal) (produced in accordance with Example I) in 0.25 mL of anhydrous ethyl ether. This mixture, protected from atmospheric moisture, was subsequently stirred at room temperature for 60 minutes, after which it was concentrated under reduced pressure to remove volatile organic material (1,4-dioxane, ether, and 1-butanol). The product (159 mg) was shown by NMR analysis to be a 3:1 mixture of the title compound and starting bisacetal, respectively. Longer reaction time failed to drive this reaction to completion, which seems to indicate that removal of the alcohol generated as the reaction proceeds is desirable.

Similar experiments were conducted using 1,4-dioxane saturated with gaseous HCl and an equal volume of various organic solvents including toluene, methylene chloride, acetonitrile, ethyl acetate, cyclohexane, and heptane. Although the desired alpha-chloro ether was obtained in all such experiments, the crude product mixture further contained unreacted starting bisacetal. Use of polar cosolvents such as acetonitrile also resulted in the formation of unidentified decomposition products.

EXAMPLE IX

Preparation of 1-Chloro-1,2,2-triallyloxyethane Using Acetyl Chloride to Generate HCl In order to generate hydrogen chloride to initiate the reaction, 190 mg (3.27 mmoles) of allyl alcohol was added to a solution of 5.00 mL (19.7 mmoles) of glyoxal bis(diallyl acetal) commercially available from Aldrich Chemical Company, Milwaukee, Wis., in 2.00 mL (28.1 mmoles) of distilled acetyl chloride. This mixture, protected from atmospheric moisture, was subsequently heated at 45° C. (external oil bath temperature) for 2 hours. Removal of the volatile organic material (allyl acetate and excess acetyl chloride) under reduced pressure afforded 4.60 g (100% yield) of the title compound, contaminated with a trace amount of unreacted bisacetal.

EXAMPLE X

Preparation of 1-Chloro-1,2,2-triethoxyethane Using Thionyl Chloride to Generate HCl To 203 mg (0.98 mmole) of glyoxal bis(diethyl acetal) (produced in accordance with Example II) was added 0.25 mL (3.4 mmoles) of thionyl chloride (97%), commercially available from Aldrich Chemical Company, Milwaukee, Wis.,; used without further purification. Since the thionyl chloride showed visible signs of containing a small amount of hydrogen chloride, presumably produced by reaction with atmospheric moisture, no attempt was made to generate more, in contrast to the experiment described in Example IV. Due to the volatility of thionyl chloride, it was used in large excess for this small-scale experiment to ensure complete reaction. As the reaction is scaled up, the quantity of thionyl chloride should be reduced—ultimately to about one equivalent. This mixture, protected from additional exposure to atmospheric moisture, was stirred at room temperature for 2.5 hours. The mixture was then diluted with 20 mL of 1:1 (volume/volume) pentane:ether; and the organic layer was washed in successive order with ice-cold 1M aqueous sodium hydroxide (20 mL) and saturated brine (20 mL's). The washed organic layer was subsequently dried over anhydrous sodium sulfate and filtered. Removal of the volatile organic material under reduced pressure afforded 191 mg (99% yield) of the title compound, shown by proton NMR analysis to be identical to the product obtained in accordance with Example IV.

EXAMPLE XI

Preparation of 1-Chloro-1,2,2-triethoxyethane Using Various Acid Chlorides to Generate HCl A mixture of 142 mg (0.69 mmole) of glyoxal bis(diethyl acetal) (produced in accordance with Example II) and 0.10 mL (0.86 mmole) of benzoyl chloride was heated at 110° C. (external oil bath temperature) for 5.5 hours, during which time the mixture was protected from atmospheric moisture. After cooling this mixture to room temperature, it was analyzed by proton NMR spectroscopy and shown to contain ethyl benzoate and unreacted benzoyl chloride, accompanied by a 2.5:1 mixture of starting bisacetal and the title compound. Although no attempt was made to optimize this reaction, presumably the addition of a catalytic amount of ethyl alcohol (to generate HCl in situ) would have accelerated the process, in analogy to the experiment described in Example IV. Additional evidence that a variety of carboxylic acid chlorides could be used in this transformation was obtained by heating a mixture of 155 mg (0.75 mmole) of glyoxal bis(diethyl acetal) and 0.25 mL (2.6 mmoles) of crotonyl chloride at 65° C. (external oil bath temperature) for 3 hours. Such conditions resulted in the virtually complete conversion of starting bisacetal to the title compound.

In a similar manner, a mixture of 198 mg (0.96 mmole) of glyoxal bis(diethyl acetal) and 0.25 mL (3.2 mmoles) of methanesulfonyl chloride was heated at 90° C. (external oil bath temperature) for 5 hours. As expected in the absence of a catalytic amount of ethanol or water (to generate sufficient HCl), reaction to yield the title compound was quite slow (approximately 10% conversion) under these conditions.

EXAMPLE XII

Preparation of 1-Chloro-1,2,2-tributoxyethane Using Thionyl Chloride to Generate HCl A mixture of 306 mg (0.96 mmole) of glyoxal bis(dibutyl acetal) (produced in accordance with Example I) and 0.25 mL (3.4 mmoles) of thionyl chloride (97%), commercially available from Aldrich Chemical Company, Milwaukee, Wis., used without purification, was stirred, while being protected from additional exposure to atmospheric moisture, at room temperature for 7.25 hours. Isolation of the product as described in the procedure of Example X afforded 264 mg (98% yield) of the title compound, shown by proton NMR analysis to be identical to the product obtained in accordance with Example V.

EXAMPLE XIII

Preparation of 1-Chloro-1,2,2-tributoxyethane Using Sulfuryl Chloride to Generate HCl A mixture of 289 mg (0.91 mmole) of glyoxal bis(dibutyl acetal) (produced in accordance with Example I) and 0.25 mL (3.1 mmoles) of sulfuryl chloride was stirred, while being protected from exposure to atmospheric moisture, at 0° C. for 60 minutes. Isolation of the product as described in the procedure of Example X afforded 270 mg of a 2:3 mixture of the title compound and unreacted bisacetal, as shown by proton NMR analysis.

EXAMPLE XIV

Preparation of 1-Chloro1,2,2-triethoxyethane Using Chlorotrimethylsilane to Generate HCl A mixture of 235 mg (1.14 mmoles) of glyoxal bis(diethyl acetal) (produced in accordance with Example II) and 0.50 ml (3.94 mmoles) of chlorotrimethylsilane was heated at 55°-60° C. (external oil bath temperature), while being protected from atmospheric moisture, for 6.25 hours. Removal of the volatile organic material at room temperature under reduced pressure afforded 230 mg of a 1:1 mixture of unreacted bisacetal and the title compound, as shown by proton NMR analysis.

EXAMPLE XV

Preparation of 1-Chloro-1,2,2-tributoxyethane Using Phosphorus Oxychloride to Generate HCl A mixture of 237 mg (0.74 mmole) of glyoxal bis(dibutyl acetal) (produced in accordance with Example I) and 0.25 mL (2.7 mmoles) of phosphorus oxychloride was stirred, while being protected from exposure to atmospheric moisture, at room temperature for 5.75 hours. Isolation of the product as described in the procedure of Example X afforded 230 mg of a mixture, shown by proton NMR analysis to include the title compound (approximately 45%), unreacted bisacetal (approximately 10%), and unidentified impurities (approximately 45%).

EXAMPLE XVI

Preparation of 1-Chloro-1,2,2-tricyclohexyloxyethane Using Thionyl Chloride to Generate HCl A mixture of 432 mg (1.02 mmoles) of glyoxal bis(dicyclohexyl acetal) (produced in accordance with Example III) and 0.25 mL (3.4 mmoles) of thionyl chloride (97%), commercially available from Aldrich Chemical Company, Milwaukee, Wis., used without purification) was stirred, while being protected from exposure to atmospheric moisture, at room temperature for 7 hours. Isolation of the product as described in the procedure of Example X afforded 398 mg of a mixture, shown by proton NMR analysis to contain the title compound (approximately 35%), unreacted bisacetal (approximately 20%), and unidentified impurities (approximately 45%).

EXAMPLE XVII

Preparation of 1-Benzoyloxy-1,2,2-triethoxyethane

A mixture of 178 mg (0.905 mmole) of 1-chloro-1,2,2-triethoxyethane (produced in accordance with Example IV) and 206 mg (1.43 mmoles) of sodium benzoate in 3.00 mL of N,N-dimethylformamide, spectrophotometric-grade, commercially available from Aldrich Chemical Co., Milwaukee, Wis., was stirred, while being protected from exposure to atmospheric moisture, at room temperature for 21 hours. The mixture was diluted with 20 mL of 3:1 (volume/volume) ether:methylene chloride; and the organic layer was washed five times with 25 mL portions of 10% aqueous sodium chloride to ensure removal of dimethylformamide. The washed organic layer was subsequently dried over anhydrous sodium sulfate and filtered. Removal of the volatile organic material under reduced pressure afforded 212 mg (83% yield) of the title compound, the identity and purity of which were ascertained by proton NMR analysis [two doublets (J=5.5 Hz), one at δ4.63 ($CH_3CH_2O$-CHOCH$_2$CH$_3$), the other at δ6.07 (CHOC(=O)C$_6$H$_5$)]. The title compound was subsequently saponified by use of potassium carbonate (2 equivalents) in 4:1 (volume/volume) methanol:water at 0° C. for 5 hours to afford glyoxal mono(diethyl acetal) and the corresponding hydrate ($CH_3CH_2O$)$_2$CHCH(OH)$_2$ and hemiacetal

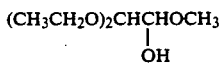

in high yield. Heating the latter mixture in toluene as described in Example XVIII affords glyoxal mono(diethyl acetal) as methanol and water are distilled out of the mixture.

A similar substitution reaction was effected using sodium acetate (in lieu of sodium benzoate) and 1-chloro-1,2,2-triethoxyethane in polar aprotic solvents such as 1-methyl-2-pyrrolidinone or dimethylformamide.

EXAMPLE XVIII

Preparation of Glyoxal Mono(Dibutyl Acetal)

A mixture of 122 mg (0.43 mmole) of 1-chloro-1,2,2-tributoxyethane (produced in accordance with Example V) and 120 mg (1.4 mmoles) of sodium bicarbonate in 2.25 mL of 8:1 (volume/volume) dimethylformamide:water was stirred at 0° C. for 2 hours. Isolation of the product as described in the procedure of Example XVII afforded 108 mg of crude glyoxal mono(dibutyl acetal), shown by spectroscopic analysis to contain a substantial amount of the corresponding hydrate ($CH_3CH_2CH_2CH_2O$)$_2$CHCH(OH)$_2$. In order to obtain the pure monoacetal derivative of glyoxal, this crude product was mixed with approximately 8 mL of toluene, followed by distillative removal (atmospheric pressure) of toluene, water, and trace amounts of 1-butanol over a period of 15 minutes until the volume of remaining solution was approximately 1 mL. Removal of residual toluene at reduced pressure afforded 77 mg (94% yield) of the named monoacetal derivative of glyoxal, whose IR and proton NMR spectral properties were consistent with those previously reported for the analogous glyoxal mono(diethyl acetal). The proton NMR of the named monoacetal exhibited doublets (J=2 Hz) at δ9.51 (aldehydic proton) and 4.55 (CHCHO). For spectral properties of glyoxal mono(diethyl acetal) (2,2-diethoxyacetaldehyde), see: H. J. Bestmann and P. Ermann, *Chem. Ber.*, 116:3264 (1983).

If one desires to prepare this monoacetal on an industrial scale, it would probably be more convenient to conduct the chlorination step (Example V), followed by this hydrolysis step, in a "one-pot" process, avoiding the need for isolating the intermediate alpha-chloro ether.

EXAMPLE XIX

Preparation of N Benzyl-2,2-diethoxyethanimine

A mixture of 158 mg (0.80 mmole) of 1-chloro-1,2,2-triethoxyethane (produced in accordance with Example IV), 0.10 mL (0.92 mmole) of benzylamine, and 136 mg (0.985 mmole) of anhydrous potassium carbonate in 1.00 mL of dimethylform-amide, spectrophotometric-grade, commercially available from Aldrich Chemical Co., Milwaukee, Wis., was stirred, while being protected from atmospheric moisture, at 0° C. for 45 minutes. Isolation of the product as described in the procedure of Example XVII afforded 146 mg (82% yield) of the title compound, whose IR and proton NMR spectral properties were consistent with the assigned structure. This transformation should prove to be quite useful for an industrial-scale synthesis of isoquinoline, previously prepared in high yield by treatment of the named imine with aqueous acid. Unfortunately, the reported preparation of this imine required using glyoxal monoacetal derivatives which are susceptible to polymerization and therefore not easily purified. See: E. Schlittler and J. Müller, *Helv. Chim. Acta*, 31:914 (1948).

The foregoing examples were provided to further illustrate various embodiments of the invention and other variations and embodiments of the examples will be readily apparent to one of ordinary skill in the art. These examples should not be used to limit the scope of this invention as is set forth in the following claims.

I claim:

1. A method for making a monochloro-glyoxal derivative of the formula

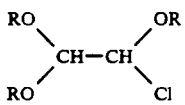

comprising the steps of:
(a) forming a first reaction mixture in the presence of a catalytic amount of acid of
  (i) glyoxal; and
  (ii) ROH wherein R is selected from the group consisting of $C_1$-$C_{10}$ alkyl, $C_5$-$C_6$ cycloalkyl, and allyl;
(b) isolating $(RO)_2CH-CH-(OR)_2$ from the first reaction mixture;
(c) forming a second reaction mixture of
  (iii) $(RO)_2CHCH(OR)_2$ and
  (iv) a chloride reagent in the presence of a catalytic amount of acid; and
(d) isolating $(RO)_2CH-CHCl(OR)$ from the second reaction mixture.

2. The method of claim 1 wherein R is $C_1$-$C_4$ alkyl.

3. The method of claim 1 wherein R is allyl.

4. The method of claim 1 wherein R is cyclohexyl.

5. The method of claim 1 wherein the chloride reagent is a catalytic amount of hydrogen chloride and a chloride containing compound selected from the group consisting of carboxylic acid chlorides, thionyl chloride, phosphorous trichloride, phosphorous oxychloride, chlorotrimethylsilane, sulfonic acid chlorides and sulfuryl chloride.

6. The method of claim 1 wherein the chloride reagent is hydrogen chloride in an aprotic solvent selected from the group consisting of dioxane, tetrahydrofuran, acetonitrile, ethyl acetate, toluene, methylene chloride, heptane, cyclohexane, and mixtures thereof.

7. The method of claim 1 wherein the chloride reagent is at least one equivalent of acetyl chloride or thionyl chloride in the presence of a catalytic amount of hydrogen chloride.

* * * * *